(12) United States Patent
Omi et al.

(10) Patent No.: US 10,578,582 B2
(45) Date of Patent: Mar. 3, 2020

(54) WIRE ROPE FLAW DETECTOR

(71) Applicant: MITSUBISHI ELECTRIC CORPORATION, Chiyoda-ku, Tokyo (JP)

(72) Inventors: Yohei Omi, Tokyo (JP); Takayuki Kotera, Tokyo (JP); Kazuyuki Yamamoto, Tokyo (JP); Takashi Yoshioka, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 60 days.

(21) Appl. No.: 15/748,837

(22) PCT Filed: Aug. 2, 2016

(86) PCT No.: PCT/JP2016/072666
§ 371 (c)(1),
(2) Date: Jan. 30, 2018

(87) PCT Pub. No.: WO2017/022764
PCT Pub. Date: Feb. 9, 2017

(65) Prior Publication Data
US 2018/0202972 A1 Jul. 19, 2018

(30) Foreign Application Priority Data
Aug. 6, 2015 (JP) .................................. 2015-156043

(51) Int. Cl.
*G01N 27/82* (2006.01)
*G01N 27/83* (2006.01)
(Continued)

(52) U.S. Cl.
CPC ............... *G01N 27/83* (2013.01); *B66B 5/00* (2013.01); *B66B 7/123* (2013.01); *B66C 13/16* (2013.01);
(Continued)

(58) Field of Classification Search
CPC ...... G01N 27/82; G01N 27/90; G01N 27/902; G01N 27/9033; G21C 17/017; G21C 17/06; H01L 2924/0002; H01L 2924/00
(Continued)

(56) References Cited

U.S. PATENT DOCUMENTS

2010/0019762 A1* 1/2010 Furusawa ............... G01N 27/83
324/240
2010/0102807 A1* 4/2010 Yoshioka ............... G01N 27/83
324/240
(Continued)

FOREIGN PATENT DOCUMENTS

JP 5-18939 A 1/1993
JP 11-230945 A 8/1999
(Continued)

OTHER PUBLICATIONS

International Search Report (PCT/ISA/210) dated Oct. 18, 2016, by the Japanese Patent Office as the International Searching Authority for International Application No. PCT/JP2016/072666.
(Continued)

*Primary Examiner* — Raul J Rios Russo
(74) *Attorney, Agent, or Firm* — Buchanan Ingersoll & Rooney PC (57) ABSTRACT

A magnetizer configured to form a main magnetic flux path so as to include a set interval in an axial direction of a wire rope includes a first pole piece and a second pole piece, which are arranged so as to sandwich the set interval therebetween, each have a U-shaped cross section which is
(Continued)

formed so as to surround the wire rope in a circumferential direction of the wire rope for about a ⅔ turn without coming into contact with the wire rope. When the wire rope is magnetized by the magnetizer, a leakage magnetic flux generated from the wire rope damaged portion is detected by a magnetic sensor.

5 Claims, 11 Drawing Sheets

(51) Int. Cl.
    *B66B 7/12*           (2006.01)
    *B66C 15/02*         (2006.01)
    *B66B 5/00*          (2006.01)
    *G01N 27/90*        (2006.01)
    *B66C 13/16*        (2006.01)
    *B66C 15/00*        (2006.01)
    *G21C 17/017*       (2006.01)
    *G21C 17/06*        (2006.01)

(52) U.S. Cl.
    CPC .............. *B66C 15/00* (2013.01); *B66C 15/02* (2013.01); *G01N 27/82* (2013.01); *G01N 27/90* (2013.01); *G01N 27/9033* (2013.01); *G21C 17/017* (2013.01); *G21C 17/06* (2013.01); *H01L 2924/00* (2013.01); *H01L 2924/0002* (2013.01)

(58) Field of Classification Search
    USPC ... 324/51, 55, 200, 219, 228, 233, 239, 254, 324/257, 260, 240
    See application file for complete search history.

(56) References Cited

U.S. PATENT DOCUMENTS

| | | | | |
|---|---|---|---|---|
| 2010/0315076 | A1* | 12/2010 | Tsukada | G01L 5/102 |
| | | | | 324/209 |
| 2014/0035569 | A1* | 2/2014 | Yoshioka | G01N 27/82 |
| | | | | 324/242 |
| 2015/0130454 | A1* | 5/2015 | Itoi | G01N 27/83 |
| | | | | 324/240 |
| 2015/0285767 | A1* | 10/2015 | Ouellette | G01R 33/04 |
| | | | | 324/240 |

FOREIGN PATENT DOCUMENTS

| | | |
|---|---|---|
| JP | 2009-122074 A | 6/2009 |
| JP | 5026440 B2 | 9/2012 |
| JP | 5420497 B2 | 2/2014 |

OTHER PUBLICATIONS

Written Opinion (PCT/ISA/237) dated Oct. 18, 2016, by the Japanese Patent Office as the International Searching Authority for International Application No. PCT/JP2016/072666.

* cited by examiner

WIRE ROPE FLAW DETECTOR

TECHNICAL FIELD

The present invention relates to a wire rope flaw detector configured to detect breakage of a wire rope used for an elevator, a crane for construction, or the like and a disconnected portion of a wire (hereinafter referred to as "wire rope damaged portion").

BACKGROUND ART

As a related-art wire rope flaw detector which is also called "rope tester", there is given a wire rope flaw detector configured to magnetize a set interval (predetermined interval) of a wire rope in an axial direction of the wire rope with permanent magnets for the wire rope running at a given speed and detect a magnetic flux leaking from a wire rope damaged portion by a magnetic sensor (coil portion) disposed in the set interval (see, for example, Patent Literature 1).

The wire rope flaw detector includes a guide path, the permanent magnets, the magnetic sensor (coil portion), and a mounting portion. The guide path has an approximately U-shaped cross section to allow passage of the wire rope. Further, the permanent magnet is disposed so as to attract the wire rope made of steel to the guide path and form a magnetic loop in the axial direction of the wire rope.

CITATION LIST

Patent Literature

[PTL 1] JP 5420497 B2 (paragraph 0040, FIG. 9, etc.)

SUMMARY OF INVENTION

Technical Problem

In order to suppress a variation in detection sensitivity, which occurs depending on a position of the wire rope damaged portion, while increasing the detection sensitivity for the wire rope damaged portion, it is desired to increase the amount of magnetic flux leaking from the vicinity of the damaged portion by the permanent magnets or electromagnets having ability of magnetizing the wire rope to an extent close to a magnetically saturated state and, at the same time, to magnetize the wire rope uniformly as much as possible.

In Patent Literature 1, the permanent magnets of the wire rope flaw detector are disposed at positions opposed to the guide path and the wire rope. Therefore, a portion of the wire rope, which is positioned in the vicinity of the permanent magnets, is relatively strongly magnetized. As a result, a portion of the wire rope, which is positioned on a side opposite to the permanent magnets, is relatively weakly magnetized. Therefore, there is a problem in that the wire rope is non-uniformly magnetized, with the result that the detection sensitivity or S/N differs depending on the position at which the wire rope damaged portion is present.

The present invention has been made to solve the problem described above, and has an object to provide a wire rope flaw detector capable of uniformly magnetizing a set interval of a wire rope to uniformize a detection sensitivity for a wire rope damaged portion and S/N so as to enlarge a range of detection for the wire rope damaged portion.

Solution to Problem

In order to attain the above-mentioned object, according to one embodiment of the present invention, there is provided a wire rope flaw detector, including: a magnetizer configured to form a main magnetic flux path so as to include a set interval in an axial direction of a wire rope; and a magnetic sensor, which is arranged in the set interval, and is configured to detect a leakage magnetic flux generated from a damaged portion of the wire rope when the wire rope is magnetized by the magnetizer, in which the magnetizer includes a first pole piece and a second pole piece, which are arranged so as to sandwich the set interval therebetween, and each have a U-shaped cross section which is formed so as to surround the wire rope in a circumferential direction of the wire rope for about a ⅔ turn without coming into contact with the wire rope, and in which a length of the first pole piece and a length of the second pole piece in the axial direction of the wire rope are equal to each other and correspond to a length in the axial direction of the wire rope that includes strands wound in the circumferential direction of the wire rope for a ¼ turn or longer, and a distance between the first pole piece and the second pole piece is set to an odd multiple of the length of each of the first pole piece and the second pole piece in the axial direction of the wire rope.

Advantageous Effects of Invention

In the wire rope flaw detector according to the present invention, the length of the first pole piece and the length of the second pole piece length in the axial direction of the wire rope are equal to each other and correspond to the length in the axial direction of the wire rope that includes the strands wound in the circumferential direction of the wire rope for the ¼ turn or longer, and the distance between the first pole piece and the second pole piece is set to the odd multiple of the length of each of the first pole piece and the second pole piece in the axial direction of the wire rope. Therefore, the set interval of the wire rope can be uniformly magnetized while holding down manufacturing cost with the magnetizer including the small pole pieces. In this manner, even when the wire rope damaged portion is formed at an unspecified position in the wire rope, uniform leakage magnetic fluxes and a uniform detection sensitivity can be obtained. Thus, the range of detection for the wire rope damaged portion can be enlarged.

DESCRIPTION OF EMBODIMENTS

First Embodiment

Figure 1A:
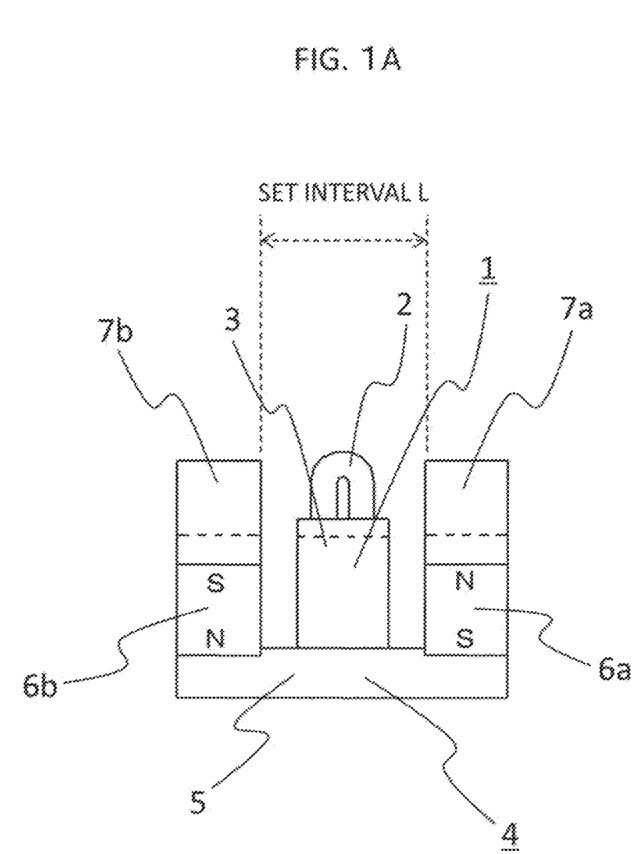
FIG. 1A is a front view for schematically illustrating a configuration of a wire rope flaw detector according to a first embodiment of the present invention.
Figure 1B:
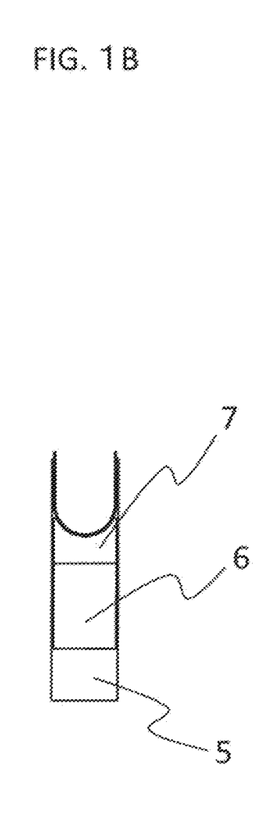
FIG. 1B is a side view for schematically illustrating the configuration of the wire rope flaw detector according to the first embodiment of the present invention.
Figure 2:
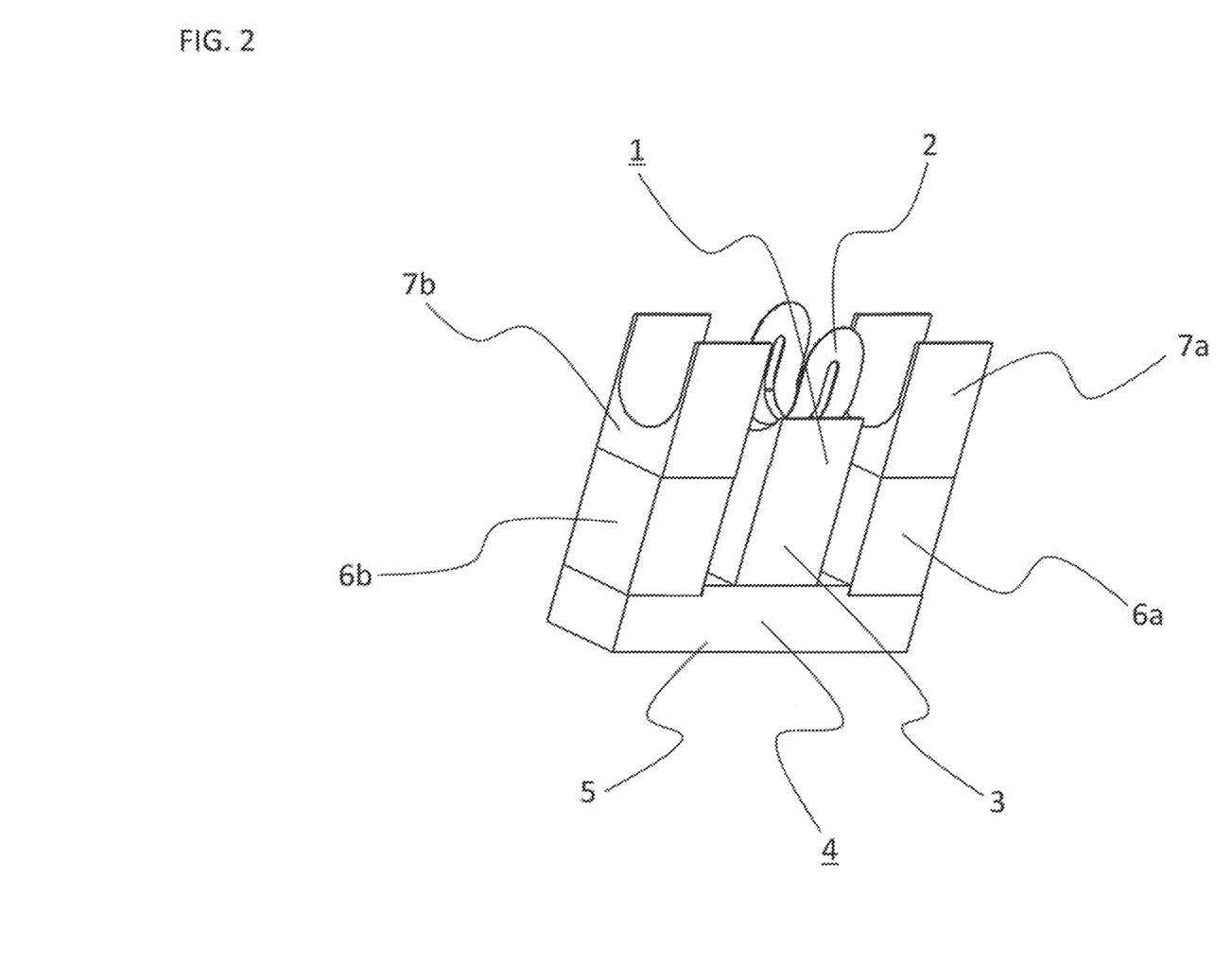
FIG. 2 is a perspective view of the wire rope flaw detector illustrated in FIG. 1A and FIG. 1B.

In FIG. 1A, FIG. 1B, and FIG. 2, a wire rope flaw detector according to a first embodiment of the present invention includes a sensor unit 1 and a magnetizer 4. The magnetizer 4 includes a back yoke 5, a pair of magnets 6a and 6b disposed at both ends of the back yoke 5, and pole pieces 7a and 7b disposed so as to be respectively adjacent to the magnets 6a and 6b, and is configured to magnetize a set interval L of a wire rope 8 in an axial direction of the wire rope 8. As illustrated in FIG. 1B, the magnets 6a and 6b are sometimes collectively referred to as "magnets 6", and the pole pieces 7a and 7b are sometimes collectively referred to as "pole pieces 7".

The set interval L described above is an interval on the wire rope 8 in the axial direction of the wire rope 8, which is sandwiched between N-S pole pairs of the magnets 6a and 6b arranged at the both ends of the back yoke 5 of the magnetizer 4, specifically, between the pole pieces 7a and 7b, as illustrated in FIG. 1A and FIG. 1B.

For the pole pieces 7, a most suitable material can be selected from metal materials (for example, iron steel such as S45C, excluding nonmagnetic materials) based on examinations of precision, durability, and cost. Each of the pole pieces 7 has a U-shaped cross section which is formed so as to surround the wire rope 8 for approximately a half turn (½ turn), as illustrated in FIG. 1B and FIG. 2.

For each of the magnets 6, a permanent magnet or an electromagnet can be selected. Further, a rectangular shape which is excellent in terms of processing cost can be used. Therefore, the magnet is not required to be formed into a U-shape as disclosed in Japanese Patent No. 5026440 (paragraph [0012]FIG. 2, and the like). Further, the magnets 6 act to magnetize the set interval L of the wire rope 8 (see FIG. 3) in combination with the pole pieces 7 so as to be adjacent thereto.

The sensor unit 1 includes a magnetic sensor 2 and a holder 3 configured to hold the magnetic sensor 2, as illustrated in FIG. 1A and FIG. 1B. As the magnetic sensor 2, a most suitable element can be selected from various elements including a detection coil, a hall element, a magneto-resistive element (MR, GMR), and a magneto-impedance element (MI) based on examinations of precision, durability, cost, and the like. In this case, the magnetic sensor 2 constructed by the detection coil is adopted. As illustrated in FIG. 2, in order to enlarge a capture range for a wire rope damaged portion as much as possible, the magnetic sensor 2 also has a U-shaped cross section which is formed so as to surround the wire rope 8 for approximately a half turn, as in the case of the pole pieces 7.

Next, a range of detection of the magnetic sensor 2 is described.

As illustrated in FIG. 1 to FIG. 4, the magnetic sensor 2 using the detection coil has a range of about 240 degrees on a cross section of the wire rope 8 as a range of detection as viewed from the wire rope flaw detector side. When the wire rope 8 passes through the magnetic sensor 2 under a non-rotating state with an axis of the magnetic rope 8 as an axis of rotation, it is assumed that a wire rope damaged portion 9 (see FIG. 4) which is present within a range of about 120 degrees on the cross section of the wire rope 8 and is positioned on the opposite side of the wire rope 8 as viewed from the magnetic sensor 2 side cannot be detected.

In practice, however, it is known that, when the wire rope 8 passes through the magnetic sensor 2, the wire rope 8 passes through the magnetic sensor 2 while rotating about the axis thereof as the axis of rotation. Therefore, when a wire rope flaw inspection is carried out for a plurality of times, the wire rope damaged portion 9 which is present in any portion of the region of the cross section of the wire rope 8 can be detected.

For the reason described above, the magnetic sensor 2 having the U-shaped cross section does not have a non-detectable region in the wire rope 8 and can have the entire region of the cross section of the wire rope 8 as the range of detection.

Next, an operation of the wire rope flaw detector according to the present invention is described with reference to FIG. 3 and FIG. 4.

Figure 3:
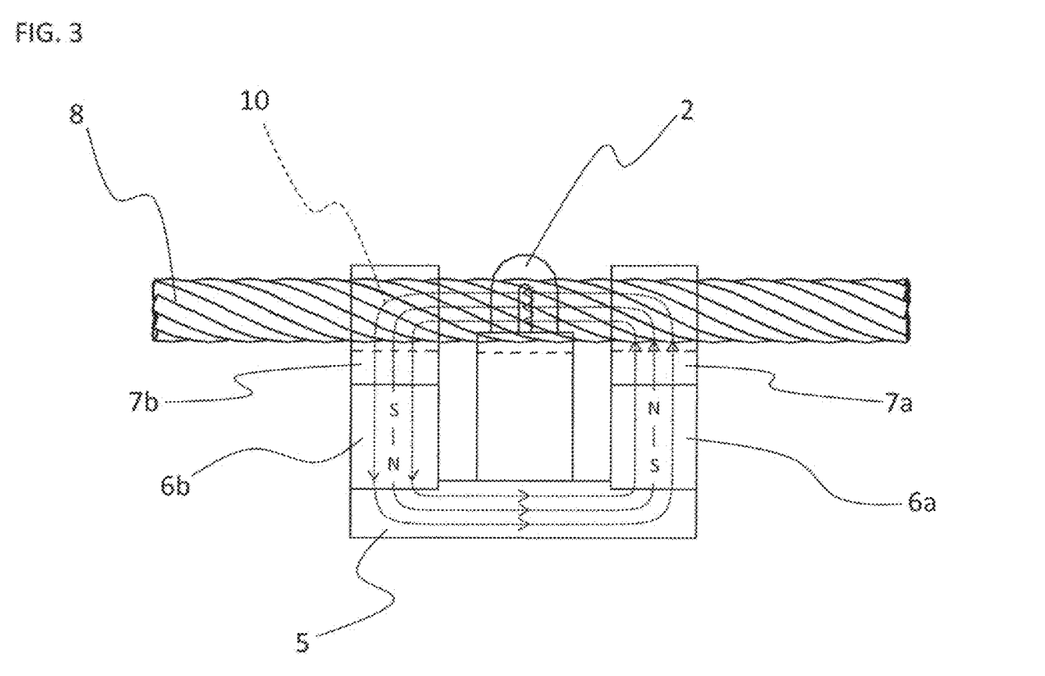
FIG. 3 is a diagram for illustrating an operation of the wire rope flaw detector illustrated in FIG. 1A and FIG. 1B when a wire rope damaged portion is not present.
Figure 4:
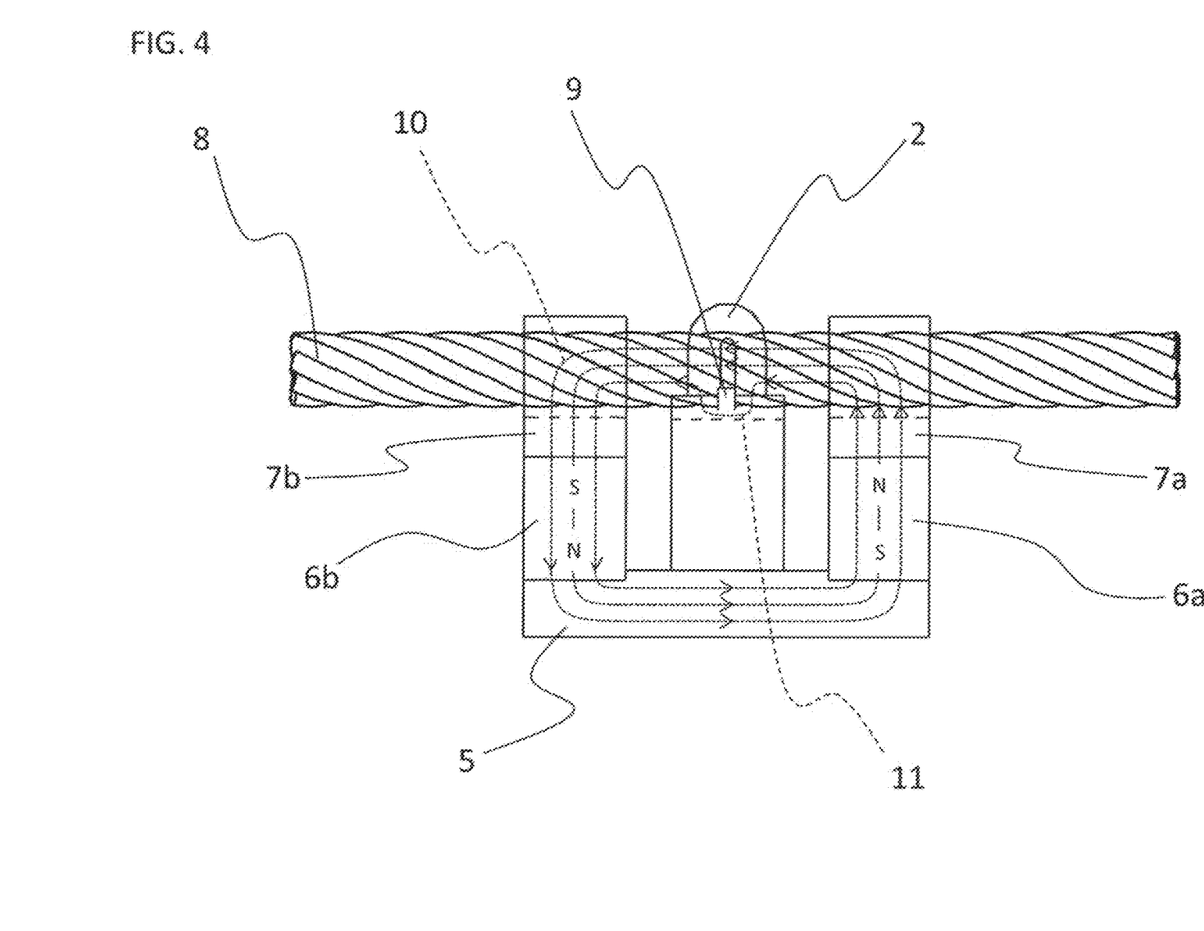
FIG. 4 is a diagram for illustrating a principle of detection of the wire rope flaw detector illustrated in FIG. 1A and FIG. 1B when a wire rope damaged portion is present.

As illustrated in FIG. 3 and FIG. 4, there is formed a magnetic circuit in which main magnetic fluxes 10 generated from the one magnet 6a of the magnetizer 4 pass via the pole piece 7a through the wire rope 8 and via the another pole piece 7b and the another magnet 6b of the magnetizer 4 and the back yoke 5 to return to the magnet 6a. A magnetomotive force of the magnetizer 4 is set so as to cause a flux density in the wire rope 8 to reach approximately a magnetic saturation and be uniform.

When the wire rope 8 has the wire rope damaged portion 9 as illustrated in FIG. 4, a leakage magnetic flux 11 is generated in the vicinity thereof. When the leakage magnetic flux 11 passes in the vicinity of the magnetic sensor 2, induced voltages are generated at both ends of the magnetic sensor 2. In this manner, the presence of the wire rope damaged portion 9 can be detected.

Next, description is made of an arrangement relationship between the wire rope flaw detector according to the present invention and the wire rope 8 being a flawed target, and uniform magnetization of a region of the wire rope 8, which is opposed to the magnetic sensor 2 (portion between the magnetic poles, specifically, portion corresponding to an axial distance between the pole pieces).

Figure 5A:
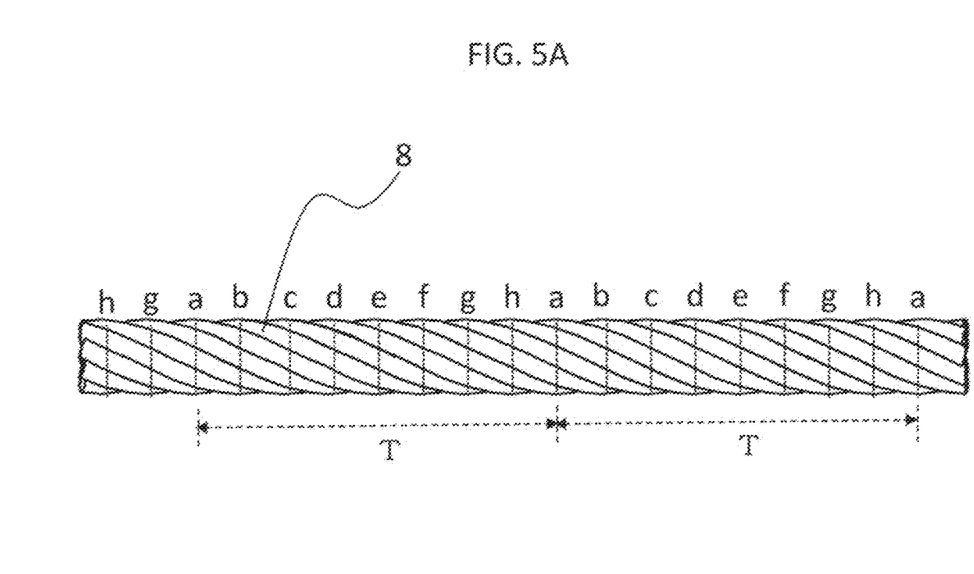
FIG. 5A is a front view for illustrating a structure of a wire rope which passes at a constant speed through the wire rope flaw detector according to the first embodiment of the present invention.
Figure 5B:
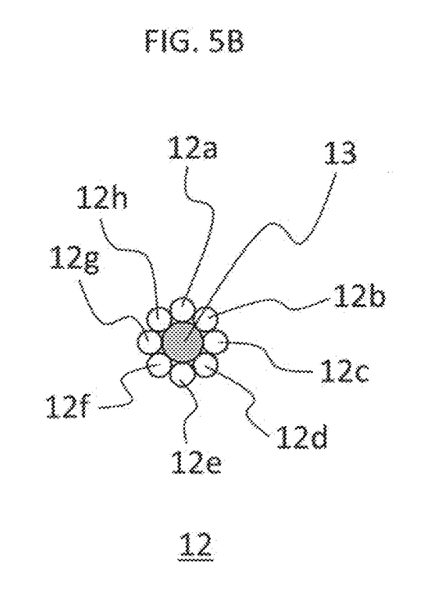
FIG. 5B is a side view for illustrating the structure of the wire rope which passes at the constant speed through the wire rope flaw detector according to the first embodiment of the present invention.
Figure 6:
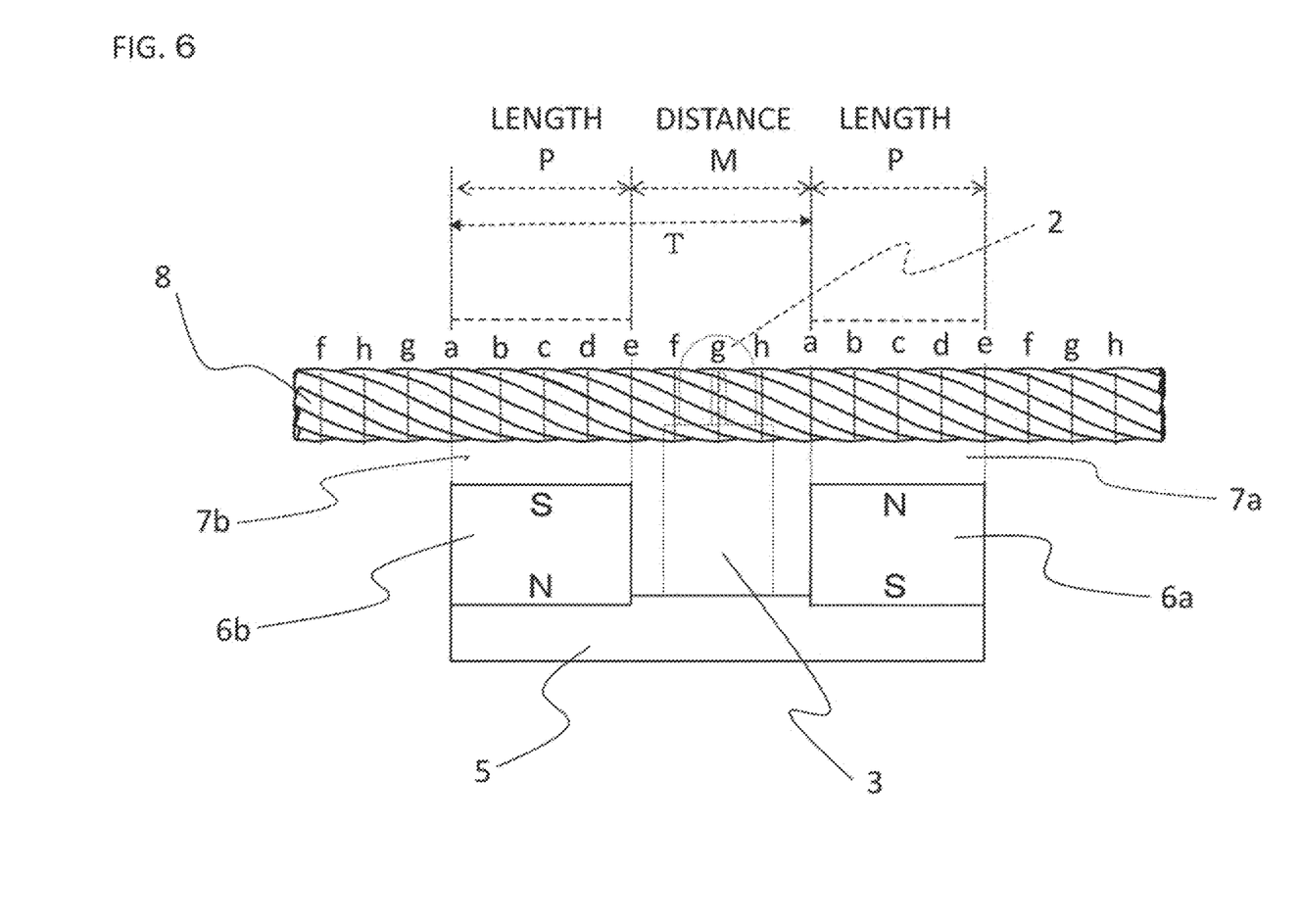
FIG. 6 is a front view for illustrating an arrangement relationship between the wire rope flaw detector according to the first embodiment of the present invention and the wire rope.

In FIG. 5A, FIG. 5B, and FIG. 6, an axial length (width) P of each of the pole pieces 7 and an axial distance M between the magnetic poles (between the pole pieces 7a and 7b) are respectively set to set lengths based on an axial periodic length T of strands 12 constructing the wire rope 8. In this manner, the pole pieces 7 and the magnets 6 are arranged, and the sensor unit 1 including the magnetic sensor 2 is arranged in the vicinity of a center between the pair of pole pieces 7a and 7b of the magnetizer 4.

As illustrated in FIG. 5A, reference symbols a to h, each denoting the respective strands 12, are assigned to positions above the wire rope 8, which correspond to hillsides of the strands 12, respectively. For clear illustration of the positions of the hillsides, directions orthogonal to the axial direction of the wire rope 8 are indicated by the broken lines.

In FIG. 5B, a cross section taken along a plane orthogonal to the axial direction of the wire rope 8 is illustrated. As the wire rope 8, the wire rope 8 formed by winding eight strands 12a to 12h around a core member 13 generally made of a fiber material, a steel material, or the like while twisting the strands 12a to 12h is used in the illustrated example. Each of the strands is generally formed by twisting together several wires or several tens of wires in a single layer or in multiple layers.

An example of the arrangement relationship between components of the wire rope flaw detector according to the present invention is illustrated in FIG. 6 based on the above-mentioned wire rope 8 illustrated in FIG. 5A and FIG. 5B.

In this example, the axial length P of each of the pair of pole pieces 7a and 7b of the magnetizer 4 is set to half of the axial periodic length T of the strands 12 so that the pole piece 7a at one end (one of the pole pieces) covers the strands 12a to 12e. The periodic length denotes a distance, for example, from the position indicated by the broken line, which corresponds to the ridge of the strand 12a, to the position indicated by the broken line, which corresponds to a next closest ridge of the strand 12a for the strand 12a, as illustrated in FIG. 5A and FIG. 6.

In this case, the pair of pole pieces 7a and 7b is arranged so that the axial distance M between the magnetic poles is equal to half of the periodic length T. Specifically, the pair of pole pieces 7a and 7b is arranged so that the axial length P of each of the pole pieces 7 and the axial distance M between the magnetic poles are equal to each other. In this manner, the pole piece 7b at another end (another pole piece) covers the strands 12a to 12e.

Figure 7A:
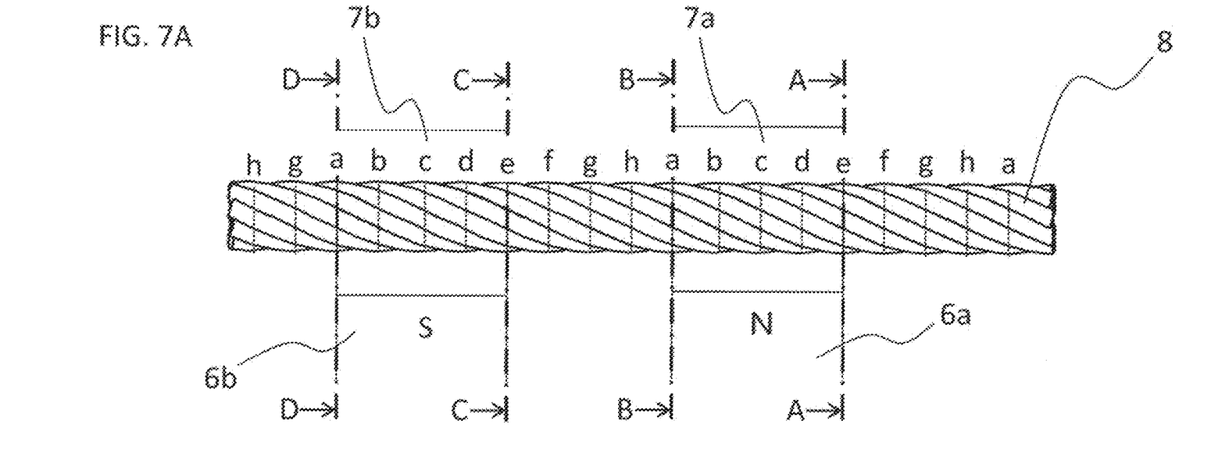
FIG. 7A is a front view for illustrating a principle of uniform magnetization of a set interval in an axial direction of the wire rope in the wire rope flaw detector according to the first embodiment of the present invention.
Figure 7B:
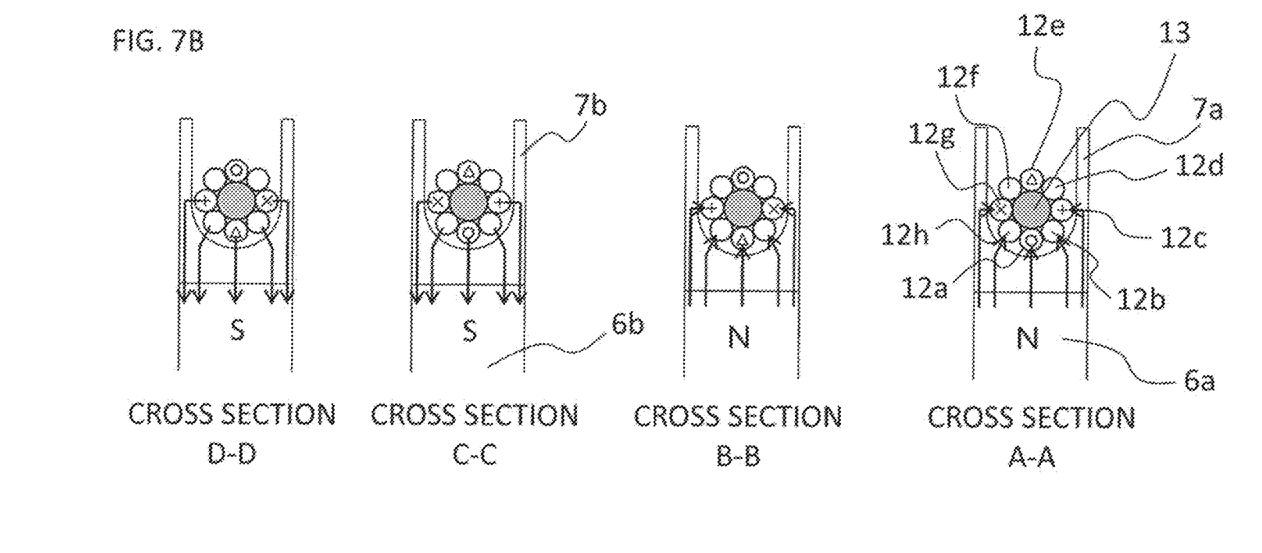
FIG. 7B is a side view for illustrating the principle of uniform magnetization of the set interval in the axial direction of the wire rope in the wire rope flaw detector according to the first embodiment of the present invention.

In FIG. 7A and FIG. 7B, a state of the magnetic fluxes flowing in the wire rope 8 is illustrated. Now, description is made of details of a principle of a uniform distribution of the magnetic fluxes flowing through the wire rope 8 in a portion of the wire rope 8 between the magnetic poles, which is sandwiched between the pair of pole pieces 7a and 7b (portion corresponding to the axial distance M between the magnetic poles in FIG. 6 and also corresponding to the set interval L illustrated in FIG. 1A).

As illustrated in FIG. 7A, the main magnetic fluxes 10 flowing out of the pole piece 7a at the one end (or the magnet 6a at the one end), which is magnetized to the N pole, can flow equally into the strands 12a, 12b, 12c, 12g, and 12h which construct the wire rope 8 as indicated by the arrows on the cross section A-A of FIG. 7B. Further, the main magnetic fluxes 10 can flow equally into the strands 12c, 12d, 12e, 12f, and 12g which construct the wire rope 8 as indicated on the cross section B-B of FIG. 7B. Specifically, the main magnetic fluxes 10 can flow equally into all the eight strands 12a to 12h which construct the wire rope 8.

Similarly, as illustrated in FIG. 7B, the main magnetic fluxes 10 flowing out of the pole piece 7a at the one end (or the magnet 6a at the one end) pass through the strands 12a to 12h between the pair of pole pieces 7a and 7b (portion corresponding to the distance M illustrated in FIG. 6) to flow into the pole piece 7b at the another end (or the magnet 6a at the another end), which is magnetized to the S pole.

In this case, the main magnetic fluxes 10 can flow equally from the strands 12a, 12b, 12c, 12g, and 12h into the pole piece 7b at the another end as illustrated on the cross section C-C of FIG. 7B and can flow equally into the strands 12c, 12d, 12e, 12f, and 12g which construct the wire rope 8 as illustrated on the cross section D-D of FIG. 7B. Specifically, the main magnetic fluxes 10 can flow equally into all the eight strands 12a to 12h which construct the wire rope 8.

As described above, the following principle is used. Specifically, a U-shaped inner surface of the pole piece 7a and a U-shaped inner surface of the pole piece 7b and a surface of the wire rope 8 are positioned in proximity to each other in semi-circular portions of the wire rope flaw detector. As a result, the main magnetic fluxes 10 can flow equally from the U-shaped inner surface of the pole piece 7a toward surfaces of the strands 12 which construct the wire rope 8. Then, the main magnetic fluxes 10 can flow equally from the surfaces of the strands 12 which construct the wire rope 8 toward the U-shaped inner surface of the pole piece 7b.

Therefore, between the pair of pole pieces 7a and 7b (in the portion corresponding to the distance NI illustrated in FIG. 6), the main magnetic fluxes 10 flowing into the strands 12a to 12h are uniform in any of the strands 12a to 12h. In this manner, over the axial distance M between the magnetic poles, the distribution of the magnetic fluxes in the wire rope 8 is uniform.

For the reason described above, the arrangement of the components which construct the wire rope flaw detector is determined so that the axial length P of each of the pole pieces 7 and the axial distance M between the magnetic poles are set equal to each other based on the periodic length T of the strands 12 which construct the wire rope 8 as a reference. Thus, the set interval L (portion corresponding to the axial distance M between the magnetic poles) of the wire rope 8 can be uniformly magnetized.

Further, the axial distance M between the magnetic poles may be set to an odd multiple of the axial length P of each of the pole pieces 7. In other words, $M=(2n-1)P$ may be satisfied, where n is a natural number. Specifically, in FIG. 7A, even when n changes, the axial position of the pole piece 7b at the another end, which is magnetized to the S pole, is at a position covering the strands 12a to 12e. Therefore, the cross section of the pole piece 7b at the another end, which is magnetized to the S pole, corresponds to the cross section C-C and the cross-section D-D. In this manner, as described above, the main magnetic fluxes 10 flowing through the strands 12 are uniform in any of the strands 12a to 12h between the pair of pole pieces 7a and 7b.

Figure 8:
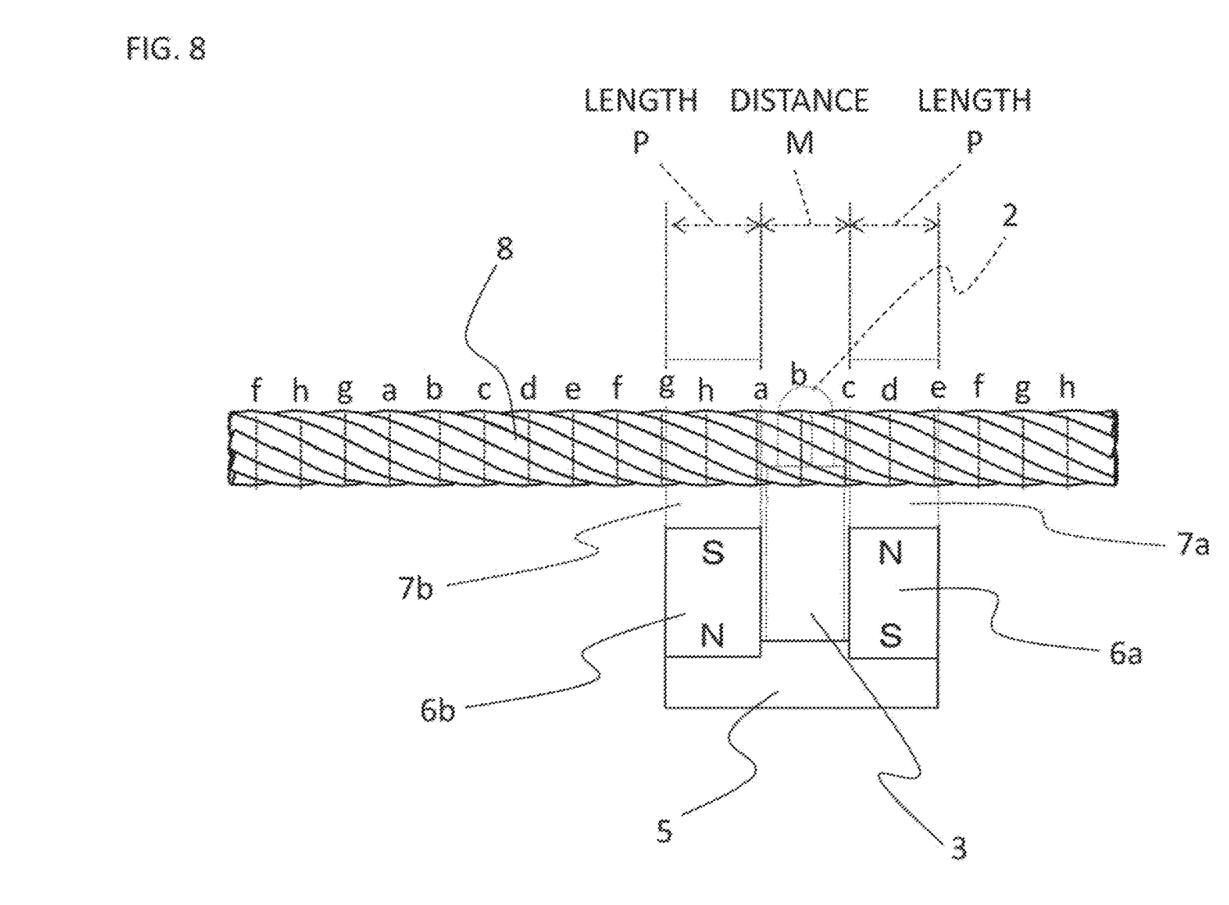
FIG. 8 is a front view for illustrating an arrangement relationship between components of the wire rope flaw detector when lengths of pole pieces in the axial direction of the wire rope are further reduced in the wire rope flaw detector according to the first embodiment of the present invention.

Next, uniform magnetization of a portion of the wire rope 8 at which the magnetic sensor 2 is arranged (portion corresponding to the axial distance M between the magnetic poles) is described based on the wire rope 8, taking an example in which the axial length of each of the pole pieces 7 in the axial direction of the wire rope 8 is reduced in the arrangement relationship of the components which construct the wire rope flaw detector according to the present invention illustrated in FIG. 8.

As illustrated in FIG. 5A and FIG. 8, the axial length P of each of the pair of pole pieces 7a and 7b of the magnetizer 4 is a length of the strands 12 along the axial direction of the wire rope 8, which are wound in the circumferential direction of the wire rope 8 for a ¼ turn so that the pole piece 7a at the one end covers the strands 12c, 12d, and 12e. At this time, the pole piece 7b at the another end is arranged so as to cover the strands 12g, 12h, and 12a by arranging the pair of pole pieces 7a and 7b so that the axial length P of the pole piece 7a and the axial distance M between the magnetic poles are set equal to each other.

Figure 9A:
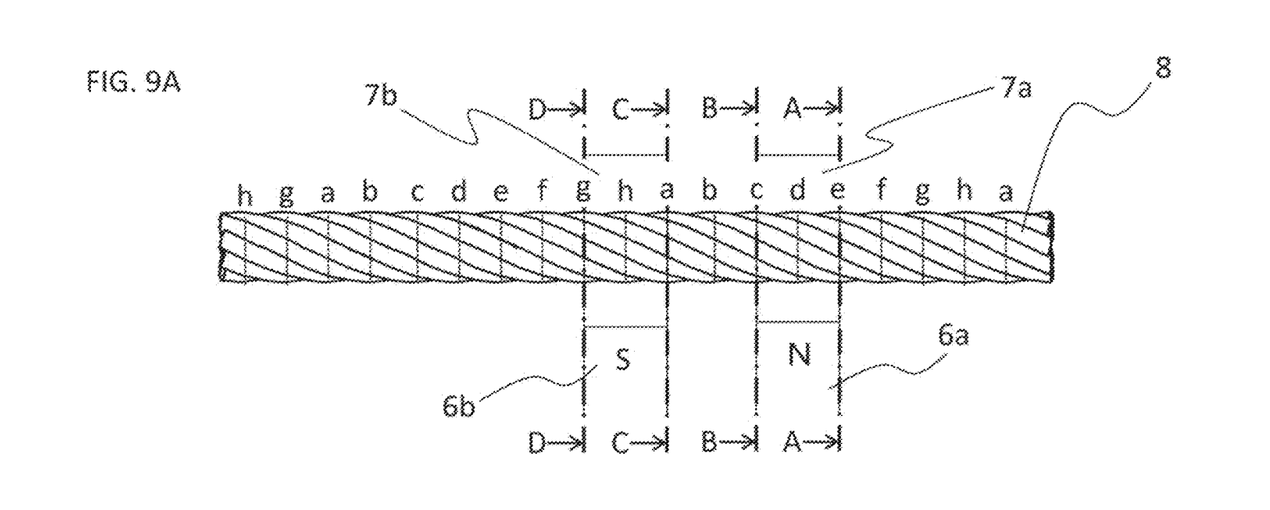
FIG. 9A is a front view for illustrating the principle of uniform magnetization of the set interval of the wire rope in the axial direction of the wire rope with the arrangement relationship illustrated in FIG. 8.
Figure 9B:
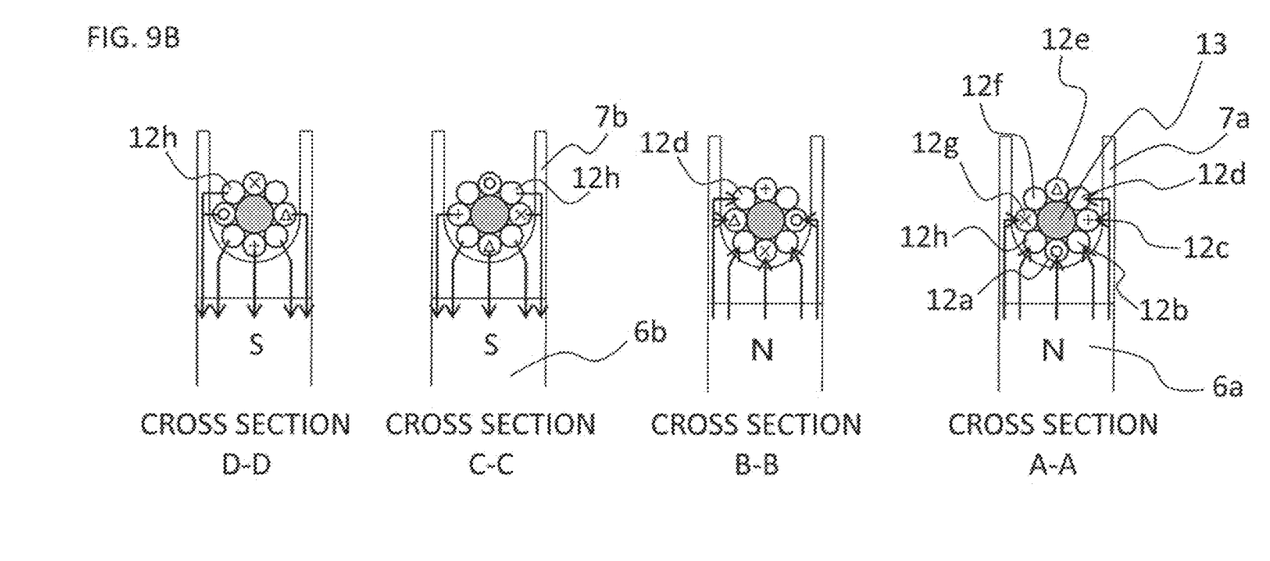
FIG. 9B is a side view for illustrating the principle of uniform magnetization of the set interval of the wire rope in the axial direction of the wire rope with the arrangement relationship illustrated in FIG. 8.

In FIG. 9A and FIG. 9B, a state of the magnetic fluxes flowing in the wire rope 8 is illustrated. Now, description is made of details of the principle of a uniform distribution of the magnetic fluxes flowing in the wire rope 8 in a portion of the wire rope 8 between the magnetic poles, which is sandwiched between the pair of pole pieces 7a and 7b of the magnetizer 4 (portion corresponding to the axial distance M between the magnetic poles in FIG. 8 and also corresponding to the set interval L illustrated in FIG. 1A).

As illustrated in FIG. 9A, the main magnetic fluxes 10 flowing out of the pole piece 7a at the one end (or the magnet 6a at the one end), which is magnetized to the N pole, can flow equally into the strands 12a, 12b, 12c, 12g, and 12h which construct the wire rope 8 as indicated by the arrows on the cross section A-A of FIG. 9B. Further, the main magnetic fluxes 10 can flow equally into the strands 12a, 12e, 12f, 12g, and 12h which construct the wire rope 8 as indicated by the arrows on the cross section B-B of FIG. 9B. Specifically, the main magnetic fluxes 10 can flow equally into all the seven strands 12a to 12c and 12e to 12h, except for the strand 12d, which construct the wire rope 8.

The surface of the strand 12d is distant from the U-shaped inner surfaces of the pole pieces 7a, and therefore a magnetic resistance becomes larger. Thus, the main magnetic fluxes 10 flowing into the strand 12d are smaller than the main magnetic fluxes 10 flowing into, for example, the strand 12a. On the cross section A-A and the cross section B-B of FIG. 9A and FIG. 9B, the main magnetic fluxes 10 flow from the U-shaped inner surfaces of the pole pieces 7a into the strand 12d at about half of a magnetic flux level.

In this manner, a magnetic flux level for one strand can be ensured in combination of the cross section A-A and the cross section B-B of FIG. 9A. Therefore, in practice, a magnitude of the main magnetic fluxes 10 flowing into the strand 12d does not greatly differ from a magnitude of the main magnetic fluxes 10 flowing into each of the other strands 12a to 12c and 12e to 12h.

Similarly, as illustrated in FIG. 9A and FIG. 9B, the main magnetic fluxes 10 flowing out of the pole piece 7a at the one end (or the magnet 6a at the one end) pass through the strands 12a to 12h between the pair of pole pieces 7a and 7b (portion corresponding to the distance M illustrated in FIG. 8) to flow into the pole piece 7b at the another end (or the magnet 6b at the another end), which is magnetized to the S pole. At this time, as indicated by the arrows on the cross section C-C of FIG. 9B, the main magnetic fluxes 10 can equally flow from the strands 12c, 12d, 12e, 12f, and 12g into the pole piece 7b at the another end.

Further, the main magnetic fluxes 10 can flow equally from the strands 12a, 12b, 12c, 12d, and 12e which construct the wire rope 8 into the pole piece 7b at the another end as indicated on the cross section D-D of FIG. 9B. Specifically, the main magnetic fluxes 10 can flow equally from all the seven strands 12a to 12g, except for the strand 12h, which construct the wire rope 8 into the pole piece 7b at the another end.

The surface of the strand 12h is distant from the U-shaped inner surface of the pole piece 7b, and therefore the magnetic resistance becomes larger. Thus, the main magnetic fluxes 10 flowing from the strand 12h into the U-shaped inner surface of the pole piece 7b become smaller than, for example, the main magnetic fluxes 10 flowing from the strand 12a into the U-shaped inner surface of the pole piece 7b. On the cross section C-C and the cross section D-D of FIG. 9A and FIG. 9B, the main magnetic fluxes 10 flow from the strand 12h into the U-shaped inner surface of the pole piece 7b at about half of the magnetic flux level. In this manner, in practice, a magnitude of the main magnetic fluxes 10 flowing from the strand 12h into the U-shaped inner surface of the pole piece 7b does not greatly differ from a magnitude of the main magnetic fluxes 10 flowing from each of the other strands 12a to 12g into the U-shaped inner surface of the pole piece 7b. This is because a magnetic flux level being substantially equal to that for one strand can be ensured on the cross section C-C and the cross section D-D, similarly to the cross section A-A and the cross section B-B of FIG. 9A and FIG. 9B described above.

Therefore, between the pair of pole pieces 7a and 7b (portion corresponding to the distance M illustrated in FIG. 6), the main magnetic fluxes 10 flowing through the strands 12 are practically uniform in any of the strands 12a to 12h. In this manner, the distribution of the magnetic fluxes in the wire rope 8 is uniform over the axial distance NI between the magnetic poles.

For the reason described above, the arrangement of the components of the wire rope flaw detector is determined so that the axial length P of each of the pole pieces 7 and the axial distance M between the magnetic poles are set equal to each other based on the periodic length T of the strands 12 which construct the wire rope 8 as a reference. In this manner, the set interval L (portion corresponding to the axial distance NI between the magnetic poles) of the wire rope 8 can be uniformly magnetized.

Further, the axial distance NI between the magnetic poles may be set to an odd multiple of the axial length P of each of the pole pieces 7, specifically, to satisfy: $M=(2n-1)P$, where n is a natural number. Therefore, as illustrated in FIG. 9A, when n=1 is given, the axial position of the pole piece 7b at the another end, which is magnetized to the S pole, is at a position covering the strands 12g to 12a. When n=2 is given, the axial position of the pole piece 7b at the another end is at a position covering the strands 12c to 12e, which is on the axially left side of the position in the case of n=1. When n=3 is given, the axial position of the pole piece 7b at the another end is at a position covering the strands 12g to 12a, which is on the further axially left side of the position in the case of n=2.

Therefore, in FIG. 9B, a cross section of the pole piece 7b at the another end, which is magnetized to the S pole, is the same as the cross section A-A and the cross section B-B when n=2 is given, except that an orientation of the main magnetic fluxes is opposite with the S magnetic pole. The cross section of the pole piece 7b at the another end is the same as the cross section C-C and the cross section D-D when n=3 is given. Therefore, as described above, between the pair of pole pieces 7a and 7b, the main magnetic fluxes 10 flowing through the strands 12 are uniform in any of the strands 12a to 12h.

A non-uniform state of the main magnetic fluxes 10 flowing through the strands 12 in the set interval L is described with reference to FIG. 10A and FIG. 10B, taking an example in which the axial length of the wire rope 8 is the shortest in the arrangement relationship of the components of the wire rope flaw detector according to the present invention.

Figure 10A:
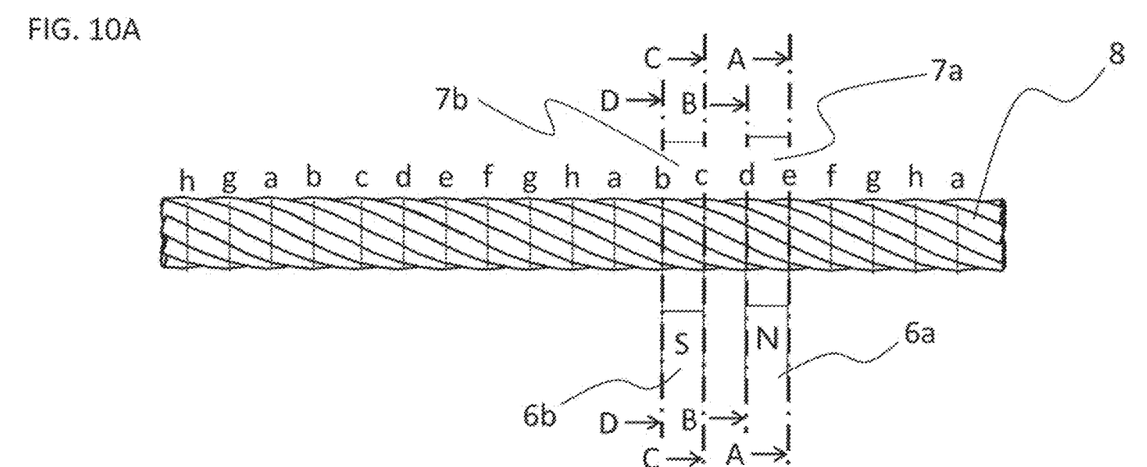
FIG. 10A is a front view for illustrating a principle of non-uniform magnetization of the set interval in the axial direction of the wire rope when the lengths of the pole pieces in the axial direction of the wire rope are minimized in the wire rope flaw detector according to the first embodiment of the present invention.
Figure 10B:
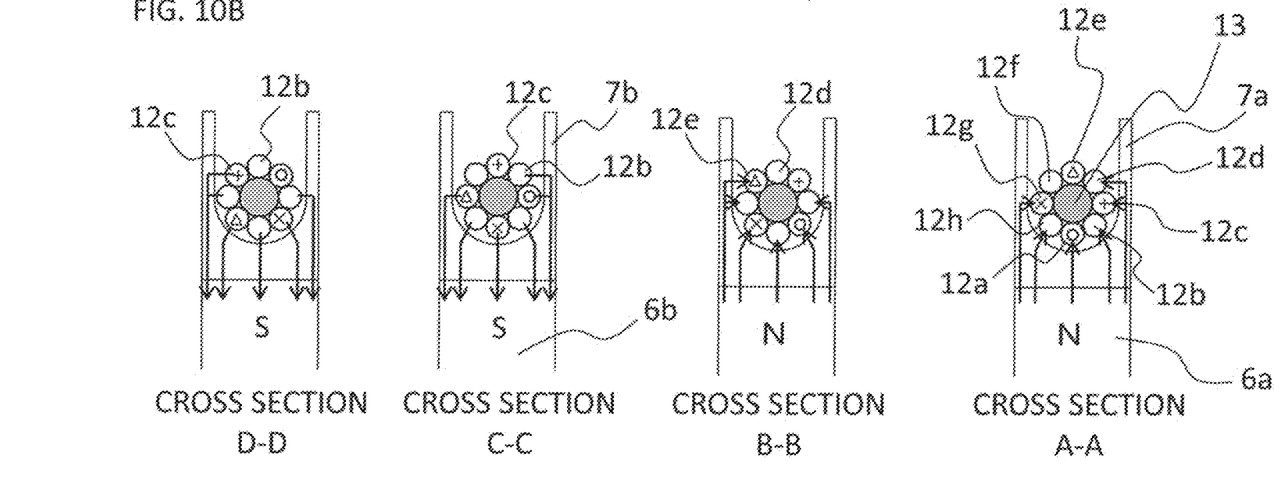
FIG. 10B is a side view for illustrating the principle of non-uniform magnetization of the set interval in the axial direction of the wire rope when the lengths of the pole pieces in the axial direction of the wire rope are minimized in the wire rope flaw detector according to the first embodiment of the present invention.

As illustrated in FIG. 10A and FIG. 1B, the axial length P of each of the pair of pole pieces 7a and 7b of the magnetizer 4 is set equal to a length of the strands 12 along the axial direction of the wire rope 8, which are wound in the circumferential direction of the wire rope 8 for a ⅛ turn so that the pole piece 7a covers the strands 12d and 12e, specifically, as illustrated in FIG. 5A, FIG. 10A, and FIG. 10B.

In this case, the pair of pole pieces 7a and 7b is arranged so that the axial distance M between the magnetic poles is set equal to ⅛ of the periodical length described above, specifically, the axial length P of the pole piece 7a and the axial distance M between the magnetic poles are set equal to each other. In this manner, the pole piece 7b at the another end is arranged so as to cover the strands 12b and 12c.

As illustrated in FIG. 10A and FIG. 10B, the main magnetic fluxes 10 flowing out of the pole piece 7a at the one end (or the magnet 6a at the one end), which is magnetized to the N pole, can equally flow into the strands 12a, 12b, 12c, 12g, and 12h which construct the wire rope 8 as indicated by the arrows on the cross section A-A of FIG. 10B. Further, the min magnetic fluxes 10 can equally flow into the strands 12a, 12b, 12f, 12g, and 12h which construct the wire rope 8 as indicated on the cross section B-B of FIG. 10B. Specifically, the main magnetic fluxes 10 can equally flow into all the six strands 12a to 12c and 12f to 12h, except for the strands 12d and 12e, which construct the wire rope 8.

On the cross section A-A of FIG. 10B, however, the surface of the strand 12e is more distant from the U-shaped inner surface of the pole piece 7a than the surface of the strand 12d, and therefore a magnetic resistance becomes larger. Thus, although compensation for the main magnetic fluxes 10 to the strand 12e on the cross section B-B of FIG. 10B is expected, only about half of the magnetic flux level is ensured even in combination of the cross section A-A and the cross section B-B. Therefore, the magnetic flux level of the main magnetic fluxes 10 corresponding to that for one strand cannot flow into the strand 12e. Therefore, the main magnetic fluxes 10 flowing into the strand 12e become smaller.

Further, on the cross section B-B of FIG. 10B, the surface of the strand 12d is more distant from the U-shaped inner surface of the pole piece 7a than the surface of the strand 12e, and therefore a magnetic resistance becomes larger. Thus, although compensation for the main magnetic fluxes 10 to the strand 12d on the cross section A-A is expected, the magnetic flux level of the main magnetic fluxes 10 corresponding to that for one strand cannot flow into the strand 12d on the cross section A-A and the cross section B-B. Therefore, the main magnetic fluxes 10 flowing into the strand 12d become smaller.

Similarly, on the cross section C-C of FIG. 10B, the main magnetic fluxes 10 flowing from the strand 12c into the U-shaped inner surface of the pole piece 7b become further smaller than the main magnetic fluxes 10 flowing from the strand 12b into the U-shaped inner surface of the pole piece 7b. Further, on the cross section D-D of FIG. 10B, the main magnetic fluxes 10 flowing from the strand 12b into the U-shaped inner surface of the pole piece 7a become further smaller than the main magnetic fluxes 10 flowing from the strand 12c into the U-shaped inner surface of the pole piece 7b. Specifically, as illustrated on the cross section C-C and the cross section D-D of FIG. 10B, the main magnetic fluxes 10 cannot flow from the strands 12b and 12c into the U-shaped inner surface of the pole piece 7b in a complementary manner.

Therefore, when the axial length P of each of the pole pieces 7 is set equal to the length of the strands 12 along the axial direction of the wire rope 8, which are wound in the circumferential direction of the wire rope 8 for the ⅛ turn, the magnetic fluxes flowing in the portion corresponding to the set interval L of the wire rope 8 vary in magnitude depending on the arrangement of the strands 12a to 12h and are non-uniform.

For the above-mentioned reason, in the arrangement relationship between the components of the wire rope flaw detector according to the present invention, the axial length P of each of the pair of pole pieces 7a and 7b of the magnetizer 4 is set equal to the length of the strands 12 along the axial direction of the wire rope 8, which are wound in the circumferential direction of the wire rope 8 for the ¼ turn (in the case of FIG. 6, FIG. 7A, and FIG. 7B). In this manner, the magnetic fluxes flowing in the set interval L of the wire rope 8 can be uniformized. Thus, the arrangement relationship with the shortest length in the axial direction of the wire rope 8 can be achieved without impairing detection sensitivity of the wire rope damaged portion 9 formed in the wire rope 8.

As described above, in the wire rope flaw detector according to the present invention, the axial length P of each of the pole pieces 7 with respect to the wire rope 8 is the length of the strands 12 in the direction along the wire rope, which are wound in the circumferential direction of the wire rope 8 for the ¼ turn or longer. The axial distance M between the magnetic poles only needs to be set to the odd multiple of the axial length P of each of the pole pieces 7, specifically, M=(2n−1)P only needs to be satisfied.

Alternatively, the axial distance M may be set to the same degrees of magnitude, specifically, M=(2n−1)P±(length along wire rope between centers of adjacent strands)/2 may be satisfied, where n is a natural number. The length along wire rope between centers of adjacent strands corresponds to, for example, a distance between d and e in FIG. 7A, specifically, a distance between a center of the strand 12d and a center of the strand 12e in FIG. 7B.

With the arrangement of the pole pieces 7 and the magnets 6 as described above, the set interval L of the wire rope 8 can be uniformly magnetized.

As a result, in the set interval L of the wire rope 8, the wire rope damaged portion 9 can be detected with the same degree of detection sensitivity regardless of the position of the wire rope damaged portion 9 in the wire rope 8.

As described above, according to the wire rope flaw detector according to the first embodiment, the magnetizer 4 including the pole pieces 7, the magnets 6, and the back yoke 5 is disposed in proximity to the wire rope 8. The axial length of each of the pole pieces 7 with respect to the wire rope 8 only needs to be set equal to the length of the strands 12 in the direction along the wire rope 8, which are wound in the circumferential direction of the wire rope 8 for the ¼ turn or longer, and the axial distance M between the magnetic poles only needs to be set to the odd multiple of the axial length P of each of the pole pieces 7.

Alternatively, the axial distance M may be set to the same degrees of magnitude of the odd multiple of the axial length P, specifically, M=(2n−1)P±(length along wire rope between centers of adjacent strands)/2 may be satisfied, where n is a natural number.

With the arrangement of the pole pieces 7 and the magnets 6 as described above, the set interval L of the wire rope 8 is uniformly magnetized so that the range of detection for the wire rope damaged portion 9 can be enlarged.

In this embodiment, when the length of each of the pole pieces 7 in the axial direction of the wire rope 8 is equal to the length in the axial direction of the wire rope 8 in a case in which the strands 12 are wound in the circumferential direction of the wire rope for the ¼ turn, the amount of used materials for the pole pieces 7 and the magnets is minimum, which is optimal in terms of manufacturing cost.

Further, when the length of each of the pole pieces 7 in the axial direction of the wire rope 8 is set equal to the length in the axial direction of the wire rope 8 in a case in which the strands 12 are wound in the circumferential direction of the wire rope 8 for the ½ turn, all the strands 12 which construct the wire rope 8 can be brought into contact with each of the two pole pieces in a similar manner. Therefore, the magnetic fluxes flowing from the N pole into the rope can flow out to the S pole without passing between the strands. Thus, the magnetic resistance is small, which is optimal in terms of efficient passage of the magnetic fluxes through the rope.

Meanwhile, when the length of each of the pole pieces 7 in the axial direction of the wire rope 8 is set larger than the length in the axial direction of the wire rope 8 in a case in which the strands 12 are wound in the circumferential direction of the wire rope 8 for the ½ turn, a detector configuration is redundant due to periodicity of the strands 12 which construct the wire rope 8.

From the description given above, although the length of each of the pole pieces 7 in the axial direction of the wire rope 8 only needs to be set to the length corresponding to the ¼ turn or longer in the circumferential direction of the wire rope 8, it is optimal in an actual configuration of the wire rope flaw detector that the length of each of the pole pieces 7 be preferably set to the length of the strands 12 in the direction along the wire rope 8, which are wound for the ½ turn or smaller.

Second Embodiment

Figure 11:
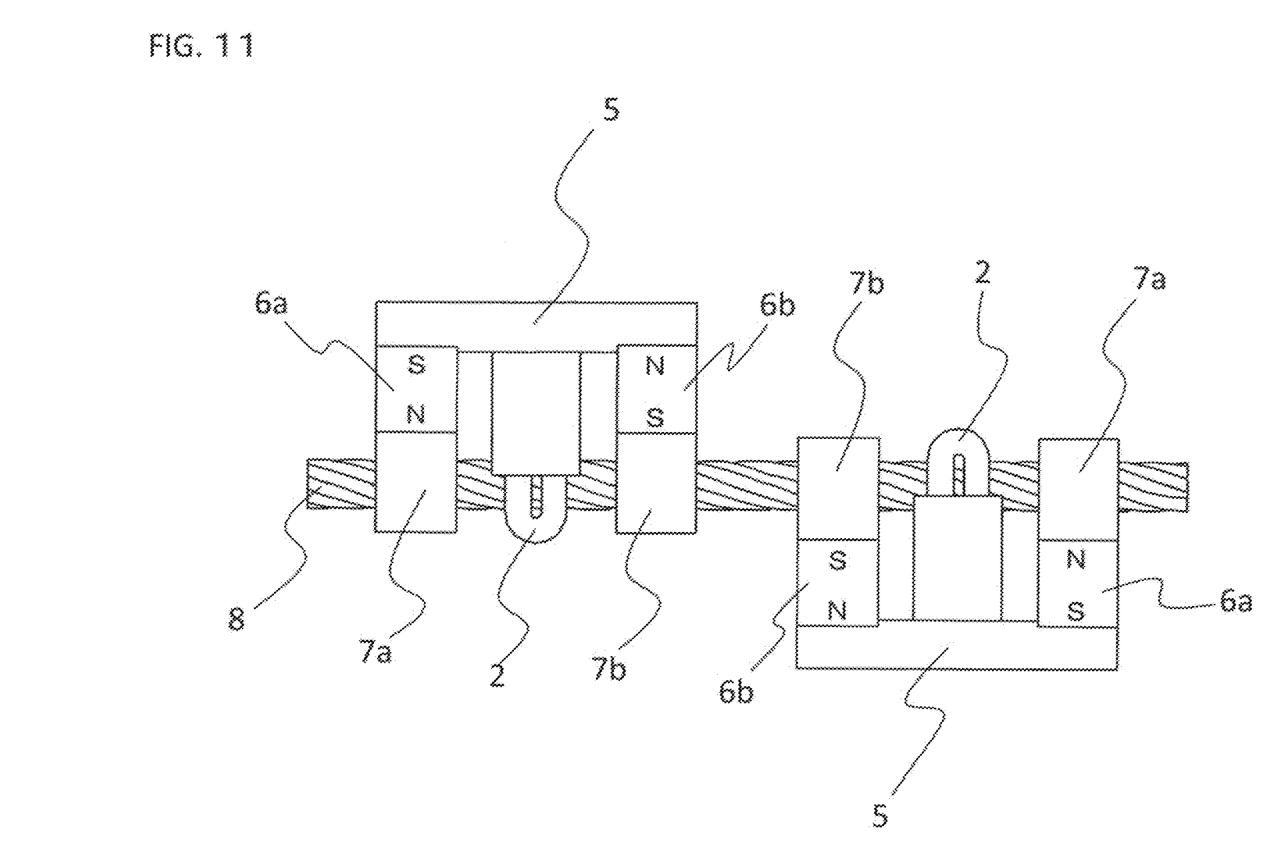
FIG. 11 is a front view for schematically illustrating a configuration of a wire rope flaw detector according to a second embodiment of the present invention.

In a second embodiment of the present invention, which is illustrated in FIG. 11, two sets of the components of the wire rope flaw detector according to the first embodiment described above are provided and are disposed with an orientation of being opposed to each other at 180 degrees with respect to the wire rope 8, specifically, so as to be sequentially oriented in opposite directions.

As described above, the two magnetizers 4 are disposed with an orientation of being opposed to each other at 180 degrees with respect to the wire rope 8. As a result, uniformity of the magnetic flux distribution in the wire rope 8 is improved.

Further, the two sensor units 1 are disposed with an orientation of being opposed to each other at 180 degrees with respect to the wire rope 8. As a result, a detection sensitivity for passage of the wire rope damaged portion through a low sensitivity region of each of the sensor units 1, specifically, through the vicinity of an opening portion of the U-shaped cross section can be mutually compensated for.

Further, when the number of magnetizers 4 disposed for each wire rope 8 is Q, the magnetizers 4 are disposed so as to be sequentially opposed at an interval of 360/Q degrees in the circumferential direction of the wire rope 8.

In this manner, an intensity of magnetization in the wire rope 8 can be uniformly increased. Thus, even when the wire rope damaged portion 9 is present in any portion in the circumferential direction of the wire rope 8, the uniform leakage magnetic flux 11 can be obtained.

Further, the above-mentioned arrangement leads to a reduction in number of inspections for the wire rope 8. Thus, not only a burden on an inspector is reduced but also inspection cost is held down.

The invention claimed is:

1. A wire rope flaw detector, comprising:
   a magnetizer configured to form a main magnetic flux path so as to include a set interval in an axial direction of a wire rope that includes strands; and
   a magnetic sensor, which is arranged in the set interval, and is configured to detect a leakage magnetic flux generated from a damaged portion of the wire rope when the wire rope is magnetized by the magnetizer,
   wherein the magnetizer includes a first pole piece and a second pole piece, which are arranged so as to sandwich the set interval therebetween, and each have a U-shaped cross section which is formed so as to surround the wire rope in a circumferential direction of the wire rope for about a ½ turn without coming into contact with the wire rope, and
   wherein a length of the first pole piece and a length of the second pole piece in the axial direction of the wire rope are equal to each other and correspond to a length in the axial direction of the wire rope that includes strands wound in the circumferential direction of the wire rope for a ¼ turn or a ½ turn, and a distance between the first pole piece and the second pole piece is set to an odd multiple of the length of each of the first pole piece and the second pole piece in the axial direction of the wire rope.

2. A wire rope flaw detector comprising:
   a magnetizer configured to form a main magnetic flux path so as to include a set interval in an axial direction of a wire rope that includes strands; and
   a magnetic sensor, which is arranged in the set interval, and is configured to detect a leakage magnetic flux generated from a damaged portion of the wire rope when the wire rope is magnetized by the magnetizer,
   wherein the magnetizer includes a first pole piece and a second pole piece, which are arranged so as to sandwich the set interval therebetween, and each have a U-shaped cross section which is formed so as to surround the wire rope in a circumferential direction of the wire rope for about a ½ turn without coming into contact with the wire rope,
   wherein the length of the first pole piece and the length of the second pole piece in the axial direction of the wire rope are equal to each other and correspond to a length in the axial direction of the wire rope that includes strands wound in the circumferential direction of the wire rope for a ¼ turn or a ½ turn, and
   wherein, where the distance between the first pole piece and the second pole piece is M and the length of the each of the first pole piece and the second pole piece in the axial direction of the wire rope is P, M=(2n−1)P±

(length along wire rope between centers of adjacent strands)/2 is satisfied, where n is a natural number.

3. A wire rope flaw detector according to claim 1, wherein the magnetizer comprises a plurality of magnetizers, and the magnetizers are disposed for each wire rope so as to be sequentially oriented in opposite directions at an interval of 360/Q (Q≥2) degrees in the circumferential direction of the wire rope, where Q is the number of magnetizers disposed for each wire rope.

4. A wire rope flaw detector according to claim 1,
wherein the magnetizer further includes, in addition to the first pole piece and the second pole piece;
a back yoke constructed of a magnetic member;
a first magnet having one end portion with one polarity held in contact with one end portion of the back yoke and in contact with the first pole piece; and
a second magnet having one end portion with another polarity held in contact with another end portion of the back yoke and in contact with the second pole piece, and
wherein the magnetic sensor has a U-shaped cross section in accordance with the U-shape of the each of the first pole piece and the second pole piece so as to allow the wire rope to pass therethrough.

5. A wire rope flaw detector according to claim 3,
wherein the magnetizer further includes, in addition to the first pole piece and the second pole piece;
a back yoke constructed of a magnetic member;
a first magnet having one end portion with one polarity held in contact with one end portion of the back yoke and in contact with the first pole piece; and
a second magnet having one end portion with another polarity held in contact with another end portion of the back yoke and in contact with the second pole piece, and
wherein the magnetic sensor has a U-shaped cross section in accordance with the U-shape of the each of the first pole piece and the second pole piece so as to allow the wire rope to pass therethrough.

* * * * *